United States Patent [19]

Harding et al.

[11] Patent Number: 4,995,066

[45] Date of Patent: Feb. 19, 1991

[54] DEVICE FOR FORMING AN X-RAY OR GAMMA BEAM OF SMALL CROSS-SECTION AND VARIABLE DIRECTION

[75] Inventors: Geoffrey Harding, Hamburg; Josef-Maria Kosanetzky, Norderstedt; Karl-Heinz Fischer; Alfred G. Meyer, both of Hamburg, all of Fed. Rep. of Germany

[73] Assignee: U. S. Philips Corporation, New York, N.Y.

[21] Appl. No.: 400,188

[22] Filed: Aug. 29, 1989

[30] Foreign Application Priority Data

Sep. 1, 1988 [DE] Fed. Rep. of Germany ....... 3829688

[51] Int. Cl.$^5$ .............................................. G21K 5/10
[52] U.S. Cl. ..................................... 378/146; 378/150
[58] Field of Search ................................. 378/146, 150

[56] References Cited

U.S. PATENT DOCUMENTS 4,745,631 5/1988 Paolini .................................. 378/146
4,750,196 6/1988 Harding .............................. 378/146
4,769,829 9/1988 Webb et al. ......................... 378/146

FOREIGN PATENT DOCUMENTS 0074021 3/1983 European Pat. Off. .

Primary Examiner—Craig E. Church
Attorney, Agent, or Firm—William Squire

[57] ABSTRACT

A device for forming an X-ray beam or gamma beam (11) having a small cross-section and a variable direction, includes an X-ray source or gamma source (1) which supplies an X-ray beam and a diaphragm device which forms the X-ray beam from the radiation beam. The diaphragm device has a stationary diaphragm section (7) provided with a rectilinear slit (8) and a cylindrical first diaphragm body (3) which rotates about an axis of rotation (5) and which is provided with a helical slit (9) on its outer surface. In order to reduce the expenditure for manufacturing a device which is also suitable for different distances between the radiation source and the axis of rotation, the diaphragm body (3) has an at least approximately semi-circular cross-section over at least a part of its length.

20 Claims, 2 Drawing Sheets

DEVICE FOR FORMING AN X-RAY OR GAMMA BEAM OF SMALL CROSS-SECTION AND VARIABLE DIRECTION

BACKGROUND OF THE INVENTION

The invention relates to a device for forming an X-ray or gamma ray beam of small cross-section and variable direction, comprising an X-ray source or gamma source which supplies a radiation beam and a diaphragm device which forms the X-ray beam from the radiation beam and which comprises a stationary diaphragm section provided with a rectilinear slit and a cylindrical first diaphragm body which rotates about an axis of rotation and which is provided with a helical slit on its outer surface.

Such devices are known from EP-OS No. 74 021 for medical applications and from, which corresponds to U.S. Pat. No. 4,750,196, for industrial applications. Therein, the diaphragm body is formed by a hollow cylinder of a radiation absorbing material, the circumference of which is provided with two mutually offset helically extending slits. When a beam of parallel rays is incident on such a diaphragm body in the direction perpendicular to the cylinder axis thereof, there will always be one point in which the X-ray beam passes through both slits. When the diaphragm body is rotated, this point travels along the axis so that a periodically moving X-ray beam emerges behind the diaphragm body. This periodically displaced X-ray beam can be used for medical or industrial examinations. The stationary diaphragm section serves to bound the X-rays perpendicularly to the direction of displacement of the X-ray beam in a defined manner.

In practice X-rays are produced by means of an X-ray tube which delivers a beam of diverging rays. In a diverging radiation beam, however, the intensity of the X-ray beam decreases towards the edges. This can be at least partly prevented by suitably shaping the slits and by ensuring that instead of extending exactly parallel to the plane formed by the rectilinear slit and the radiation source, the axis of rotation of the diaphragm body encloses an angle with respect thereto which angle depends on the divergence of the radiation beam, i.e. on the distance between the radiation source and the axis of rotation of the diaphragm body.

Therefore, such a diaphragm body can be manufactured only at considerable expenditure and is suitable only for one given distance between the radiation source and the axis of rotation.

SUMMARY OF THE INVENTION

It is an object of the present invention to provide a device of the kind set forth which produces a reciprocating primary beam in a different manner.

This object is achieved in accordance with the invention in that the diaphragm body has an at least approximately semi-circular cross-section over at least a part of its length.

Thus, in accordance with the invention the X-ray beam is formed from the (diverging) X-ray beam by cooperation of a helical slit in the first diaphragm body and a rectilinear slit in a stationary diaphragm section. The point of emergence of the X-ray beam is displaced by rotation of the first diaphragm body, resulting in a periodically moving X-ray beam. Because the X-rays emerge through a slit instead of through two oppositely situated slits in the diaphragm body, the intensity of the X-ray beam does not decrease towards the ends of the diaphragm body. Therefore, it is not necessary to impart a given shape to the slit or to arrange it in a defined manner with respect to the rectilinear slit.

The cooperation of the slits in the stationary diaphragm section and the diaphragm body defines an X-ray beam having a trapezoidal cross-section. However, it is desirable to obtain a square (or circular) cross-section which would produce a direction-independent spatial resolution. For the same width of the two slits, the approximation of the square cross-section is better as the angle at which the projection of the two slits intersect one another becomes larger, e.g. approaches 90°. A larger angle of intersection could be achieved by using a diaphragm body having a large diameter and a small axial length. For many applications, however, a comparatively large deflection angle is required for the X-ray beam, implying a corresponding axial length of the diaphragm body; because of the inherently large volume, a large diameter is undesirable for many applications.

In order to achieve an attractive beam cross-section also in the case of a diaphragm body having a comparatively large axial length and a comparatively small diameter, in a further version of the invention a plurality of helical circumferential slits are provided in the first diaphragm body so that they overlap one another in the axial direction. In the case of n slits in the first diaphragm body, each slit extends over only 1/n of the length of the diaphragm body, so that the projection of the helical slits in the diaphragm body on the diaphragm section intersect the slit provided therein each time at a comparatively large angle, resulting in an attractive cross-sectional shape.

The n helical slits produce n X-ray beams which, in response to one half revolution of the diaphragm body, travel each time to a position which was occupied by a neighbouring X-ray beam at the beginning. For different applications, for example for applications where the scattered radiation produced by the X-ray beam is measured as described in DE OS No.34 43 095, however, the use of a single X-ray beam only is desired.

A further version of the invention which is suitable for this purpose is characterized in that there is provided a second diaphragm body which has a semicircular cross-section over at least a part of its lenght, the two diaphragm bodies being coaxially arranged so that one encloses the other, the first diaphragm body rotating faster as a function of the number of slits provided therein with respect to the second diaphragm body, the arrangement and the shape of the aperture (apertures) on the circumference of the second diaphragm body being such that a usable beam can emerge each time from only one of the slits (for example 9b).

In the simplest version of this embodiment in accordance with the invention a helical slit is provided as the single aperture in the second diaphragm body, which slit is substantially wider than the slits in the first diaphragm body and extends over a circumferential angle of at least approximately 180°. The slits are thus successively traversed in the course of one half revolution of the second diaphragm body, the X-ray beam continuously moving from one side to the other. Because the number of revolutions of the first diaphragm body is higher than that of the second diaphragm body, one slit in the first diaphragm body will be traversed when the slit or the diaphragm body faces the radiation source, a neighbouring slit being traversed when it or the diaphragm body is remote from the radiation source. The X-ray beam then produced is wider in the first case than in the second case, the differences being greater as the diameter of the diaphragm body is greater with respect to its distance from the radiation source.

In order to prevent the X-ray beam from being alternately wider and narrower in cases where the above condition is not satisfied in a further embodiment in accordance with the invention n apertures are provided in the second diaphragm body, n being the number of slits in the first diaphragm body, the apertures being offset through an angle of 180°/n on the circumference, their axial position corresponding to the axial position of each time one slit so that the radiation passes each time through the slit via the associated aperture.

In this respect it is assumed that the X-rays are switched off each time when the slits in the first diaphragm body face the radiation source.

BRIEF DESCRIPTION OF THE DRAWING

The invention will be described in detail hereinafter with reference to drawings. Therein.

DETAILED DESCRIPTION OF THE PREFERRED EMBODIMENTS

Figure 1:
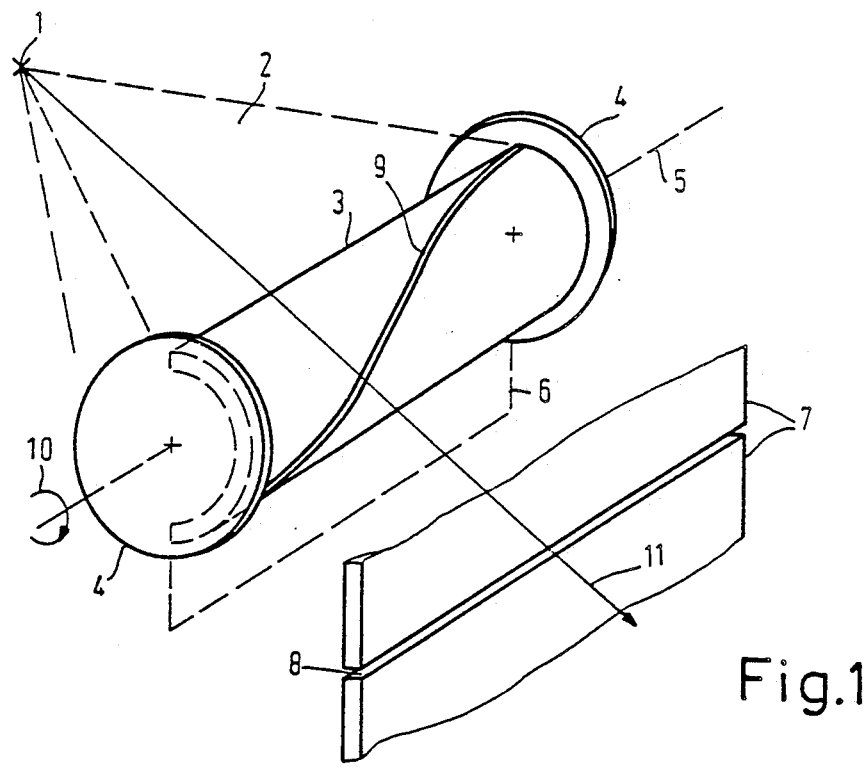
FIG. 1 shows a first embodiment in accordance with the invention.

The reference numeral 1 in FIG. 1 denotes the focus of an X-ray tube, (not shown) which emits an X-ray beam 2 which is denoted by broken lines. The X-ray beam 2 is incident on a diaphragm body 3 which is formed by a hollow cylinder having a semi-circular cross-section. At its end faces the diaphragm body is supported by circular discs 4. The discs 4 are rotatable about an axis of rotation 5 by a motor (not shown) on which the centres of curvature of the inner surface of the hollow cylinder 3 are situated. As is denoted by the broken line 6, the discs 4 are immobile in the axial direction. This can be achieved, for example by journalling the discs 4 so as to be rotatable about the axis 5 in a respective bearing which is arranged in a housing (not shown) which is connected to the X-ray source.

The diaphragm body 3 is made of such a material and has such a thickness that the X-rays are substantially completely absorbed thereby. The thickness and the material of the diaphragm body depend on the intensity of the X-rays. For an X-ray tube voltage of 120 kV, a diaphragm body consisting of tungsten or a tungsten alloy and having a thickness of 1.5 mm absorbs the X-rays substantially completely. The thickness of the body 3 is limited to a value $d_m$ which results from the relation $$d_m = w/\tan(\beta/2),$$

where $\beta$ is the deflection angle of the X-ray beam and w is the width of the X-ray beam. For a deflection angle of, for example 23° and w=0.5 mm, $d_m$=2.45 mm.

The diaphragm body 3 is provided with a helical slit 9 which connects one corner of the diaphragm body (top right) to the oppositely situated corner (bottom left). The width of the slit is adapted to the size of the X-ray beam to be formed.

On the other side of the diaphragm body (viewed from the focal point 1) there is arranged a stationary diaphragm plate 7 which comprises a rectilinear slit 8. The radiation source 1, the diaphragm body 3 and the diaphragm plate 7 are preferably so arranged with respect to one another that the axis of rotation 5 of the diaphragm body is situated in the plane defined by the central line of the slit 8 and the focus 1 and extends parallel to the plane defined by the diaphragm 7. The focus 1 should be situated as well as possible in the symmetry plane of the diaphragm body 3 and the diaphragm plate 7, which plane extends perpendicularly with respect to the axis of rotation.

The X-ray beam 2 passes through the slit 9 in the diaphragm body at the area where the slit 9 is intersected by the plane defined by the axis of rotation 5 and the focus 1, as well as at a given area around this point of intersection. The diaphragm plate 7, however, transmits only the X-ray beam emerging from the point of intersection and substantially suppresses the X-rays emerging on both sides of this beam from the slit 9, i.e. above and below the plane defined by focus 1 and slit 8, so that an X-ray beam 11 having a small cross-section (pencil beam) emerges from the slit 8. Between source 1 and the device comprising body 3 and plate 7, there is arranged a diaphragm (not shown) which prevents radiation from emerging while by-passing the diaphragm device.

In response to a rotation of the diaphragm body 3 about the axis 5 in the direction denoted by the arrow 10, the point of intersection between the plane defined by focus 1 and slit 8 and the slit 9 is displaced to the right, so that the X-ray beam 11 also travels to the right until the end of the slit 9 is reached. When the diaphragm body 3 is rotated further, the X-ray beam first traverses the left hand end of the slit 9 and subsequently moves to the right again, so that a periodic sawtooth-shaped motion of the X-ray beam is obtained when the diaphragm body is rotated at a constant speed.

The period of time elapsing between the end of the motion (right) and the beginning anew (left) on the one hand depends on the circumferential angle described by the slit 9 on the diaphragm body and on the other hand on the arc described by the cross-section of the body itself. If the period is to be short, the arc may be only slightly larger than 180° and the angle described by the slit 9 on the circumference of the diaphragm body must be 180°. The arc may not be made exactly equal to 180° because in the angular position of the diaphragm body in which the diaphragm body 3 edge occupies the angular position defined by the axis of rotation 5 and the focus 1, X-rays would emerge from the slit 8 while by-passing the diaphragm body 3. Consequently, the arc of the circular cross-section of the diaphragm body 3 must be slightly larger than 180°, so that the slit 8 is always shielded from the focus 1 by the diaphragm body 3 until the position is reached in which the X-ray beam 11 traverses the slit 9.

Figures 2, 3:
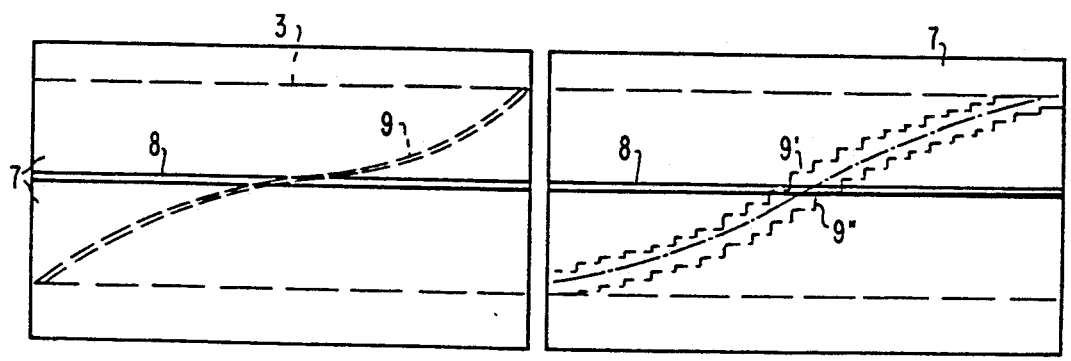
FIG. 2 shows the diaphragm body and the diaphragm section of a first embodiment.
FIG. 3 shows the diaphragm body and the diaphragm section in a second embodiment.

It has been assumed thus far that the slit 9 has a helical shape, i.e. that its pitch is constant over the entire length of the body 3. In many cases, however, it is desirable that the beam 11 is moved faster (or slower) at the centre than at the edge. Such an embodiment is shown in FIG. 2 which shows the stationary diaphragm plate 7 and the diaphragm body 3 from side of the diaphragm plate 7. It appears that the pitch of the slit (viewed in the axial direction) is greater in the centre than at the edge. Consequently, in the case of a constant rotary speed of the diaphragm body, the X-ray beam moves faster at the centre than at the edges of the slit 9.

FIG. 3 shows an embodiment in which the slit 9 is formed by two stepped curves 9' and 9, the width-to-height ratio being the same for all steps and corresponding to the ratio of the length of the diaphragm body to its circumference. In this embodiment the X-ray beam formed is not moved continuously but intermittently. This is advantageous for various applications, for example for applications where the intensity of the primary beam (on the other side of the examination zone) is measured by means of a plurality of adjacently arranged detectors.

When the diaphragm body forms an integral unit, the angle described by the cross-sectional arc of the diaphragm body must always be larger (for mechanical reasons) than the circumferential angle described by the slit. This prolongs the period of time elapsing between the disappearance of the X-ray beam (at the right hand end) and its re-emergence (at the left hand edge). Moreover, it is comparatively complex to form a slit in an integral diaphragm body, notably when a stepped shape as shown in FIG. 3 is required.

These drawbacks can be avoided by manufacturing the diaphragm body from two matching sections which are separated by the slit and whose end faces are rigidly connected to the discs 4 in which they are preferably inserted into segment shaped grooves provided therein. The desired course of the slit 9 can then be comparatively simply realised by suitable working of the facing surfaces of the two sections forming the diaphragm body.

Because the central projection (as from the focus 1) of the slit 9 on the diaphragm plate 7 intersects the slit 8 at an angle other than 90°, the cross-section of the X-ray beam 11 will be greater in the direction of the slit than in the direction perpendicular thereto, even though the width of the slits 8 and 9 is the same. This difference is greater as the diameter of the diaphragm body 3 is smaller and its length is greater.

A more distinct lateral delimitation could be achieved by tilting the axis 5 out of the plane defined by the focus 1 and the slit 8, i.e. so that the right hand side of the diaphragm body is raised and the left hand side is lowered. This is because the angle between the central projection of the slit 9 and the slit 8 would then be larger so that the X-ray beam 11 would be somewhat more strictly defined in the lateral direction. However, the arc of the diaphragm body 3 should then be prolonged even further beyond 180° in order to prevent X-rays from reaching the slit while bypassing the diaphragm body in a given position.

Figure 4:
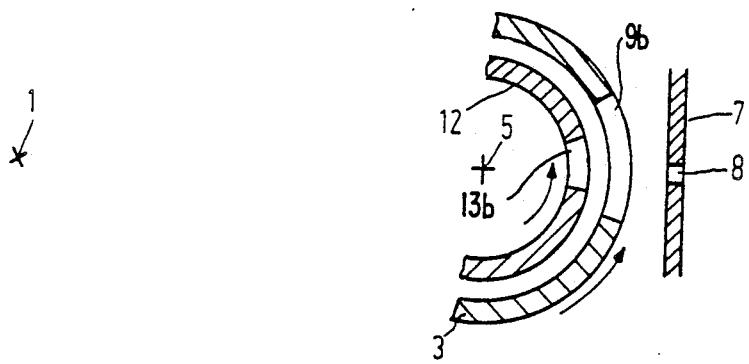
FIG. 4 is a cross-sectional view of a preferred embodiment.

FIG. 4 shows a preferred embodiment which produces a substantially better lateral delimitation of the X-ray beam 11 formed for the same length and the same diameter of the diaphragm body. Instead of only one diaphragm body, between the radiation source 1 and the diaphragm section 7 there are arranged a first diaphragm body 3 and a second diaphragm body 12, which bodies are coaxially arranged so that one enclose the other. The two diaphragm bodies again have a semi-circular cross-section over at least a part of their length which may amount to, for example 50 mm. Like in the device shown in FIG. 1, between the radiation source 1 and the diaphragm device there is arranged a diaphragm (not shown) which prevents radiation from emerging while by-passing the diaphragm device.

Figure 5:
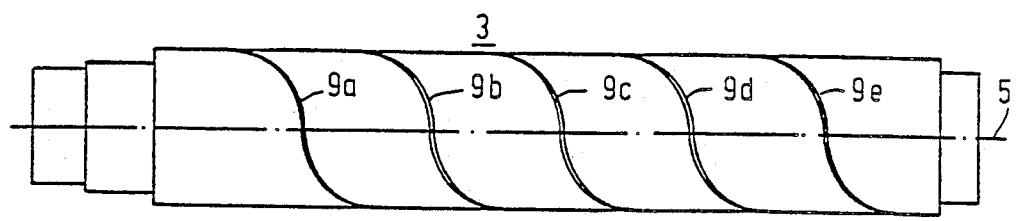
FIGS. 5 and 6 are plan views of the first and the second diaphragm body, respectively, of the embodiment shown in FIG. 4, and FIGS. 7 and 8 show a development of the first and the second diaphragm body, respectively.
Figure 7:
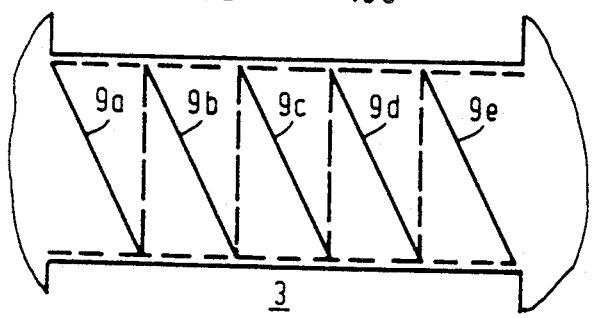

The first diaphragm body 3, enclosing the second diaphragm body 12, is shown in FIG. 5 as well as in a development in FIG. 7. This first diaphragm body comprises 5 slits $9a \ldots 9e$ which have a width of, for example 0.4 mm. However, a different number of slits may also be provided, be it that this number be odd. As appears from FIG. 7, the slits $9a \ldots 9e$ all have the same, constant pitch. In the axial direction each of the slits extends over one fifth of the length of the zone of semi-circular cross-section. A given overlap then exists between the areas occupied by the slits in the axial direction, i.e. one slit already commences when the neighbouring slit has not yet completely terminated. Thus, all positions within the deflection angle of the X-ray beam, determined by the construction, are irradiated by a beam 8. The cross-section through the first body 3 describes an arc of circle of exactly 180°. In order to ensure that the slits do not slice up the diaphragm body, they extend through a circumferential angle which is slightly smaller than 180°, for example 170°, as appears from FIG. 7.

Figure 6:
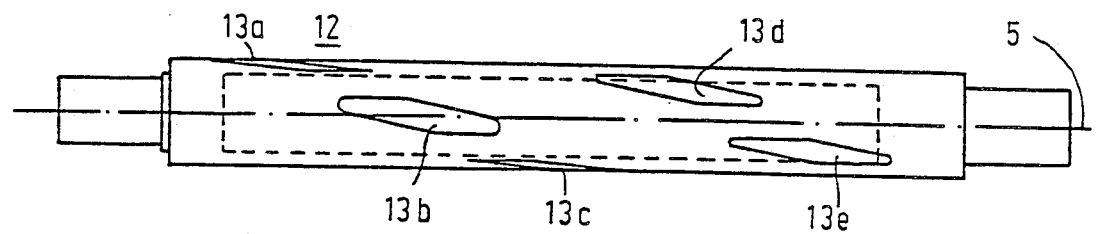
Figure 8:
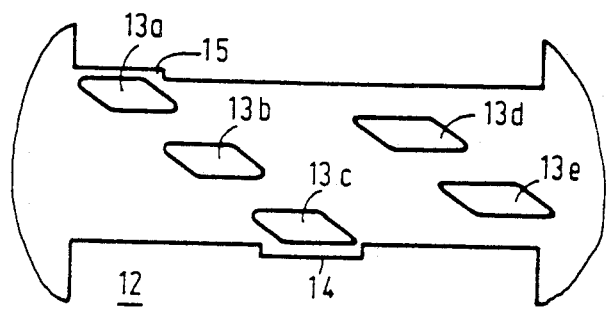

FIGS. 6 and 8 show that the inner, second diaphragm body 12 which is shown in a plan view and a development, respectively, comprises trapezoidal apertures $13a \ldots 13e$ whose number corresponds to the number of slits in the first diaphragm body; in the example, therefore, there are five apertures. Each aperture extends in the axial direction across a region whose central projection on the first diaphragm body 3 has a length which at least equals that of a slit in the first diaphragm body (in the axial direction). Each of the apertures $13a \ldots 13e$ extends across a circumferential angle which is wider than one fifth of the circumferential angle described by the slits $9a \ldots 9e$ in the first diaphragm body, for example through 36°. The apertures are offset on the circumference by 180°/5, i.e. by 36°. The aperture $13a$ associated with the slit $9a$ extends through an angular range of from 0° to 36°. The aperture $13b$ associated with the second slit $9b$ extends through the angular range from 72° to 108° and the third aperture $13c$ which is associated with the slit $9c$ extends through an angular range of from 144° to 180°. The aperture $13d$ covers the angular range from 36° to 72° and the aperture $13e$ covers the range from 108° to 144°. Portions 14 and 15 at the area of the outer apertures $13a$ and $13c$ close off the apertures from the surroundings.

The outer diameter of the diaphragm bodies 3 and 12 may amount to, for example, 12.5 mm and 8.4 mm, respectively, and their axial length in which slits or apertures are provided amounts to approximately 50 mm. It is to be noted that the FIGS. 4, 5, 6, 7, 8 show these diaphragm bodies each time at a different scale.

During operation, the diaphragm bodies rotate in the same direction, the angular speed of the first diaphragm body being five times higher than that of the second diaphragm body. This can be achieved by providing the end faces of the diaphragm bodies with toothed portions (not shown) which are coupled to a common drive motor, the gear ratio being chosen accordingly for the two diaphragm bodies. Instead, however, for each diaphragm body there may also be provided a separate stepping motor, the motor for the first diaphragm body receiving five times as many drive pulses for the same step width, or the same number of pulses when the step width is five times larger.

It is assumed that at a given instant during operation the slits 9a . . . 9e face the diaphragm plate 7 and that the focal spot is situated in a plane which extends perpendicularly to the plane of drawing and which contains the axis of rotation 5. In this case an X-ray beam can pass through the aperture 13b, the slit 9b and the slit 8 in the diaphragm plate 7. All other slits (more accurately speaking, the parts of these slits which are situated in the plane defined by the source 1 and the axis 5) are shielded by the diaphragm body 12. Under the influence of the rotation, the point of intersection of the slit 9b and the latter plane is shifted to the right, i.e. the X-ray beam travels to the right, the aperture 13b being moved upwards at the same time until the end of the slit 9b is reached. The X-ray beam then emerges just from the lower area of the aperture 13b.

When the end of the slit 9b has been reached in this manner, the beam through the slit 9b is interrupted by further rotation and the front edge (with respect to the direction of rotation) of the first diaphragm body 3 intersects the latter plane. Subsequently, radiation passes through another slit, that is to say the slit whose associated aperture succeeds the aperture in the circumferential direction which has last been irradiated. In the present embodiment, this would be the slit 9e and the aperture 13e. However, the slit 9e would then face the radiation source 1, i.e. it would be situated between the radiation source and the axis 5, while the slit 9b was previously situated on the other side of the axis 5. For an equal slit width, the cross-section of the X-ray beam would thus be increased. This variation of the width of the X-ray beam formed can itself still have a disturbing effect when the distance between the radiation source 1 and the axis 5 amounts to, for example 110 mm in the case of an outer diameter of the diaphragm body 3 of 12.5 mm.

In order to avoid the described widening of the X-ray beam, the X-rays are switched off until the front edge of the diaphragm body 3 is situated underneath the plane defined by focus 1 and axis 5. Switching off can be controlled by an angle detector (not shown) which is coupled to the diaphragm body 3.

When the front edge of the diaphragm body 3 passes through the latter plane in the upwards direction, the upper edge of the aperture 13c is also situated in this plane. This aperture subsequently passes the beam passed by the slit 9c and the X-ray beam emerging through this slit again moves to the right. Because of the described overlapping of the slits 9a . . . 9e in the axial direction, the X-ray beam emerges at the same position, with respect to the plane, in which it emerged upon reaching the end of the slit 9b, or slightly to the left thereof. As a result, the dose of the X-ray beam in the overlapping zone could be higher than that outside this zone because the X-rays at the end of the slit 9b and at the beginning 9c are summed. This effect, however, can be compensated for when in this position of the X-ray beam defined by the angle detector, the measurement values of the detector device (not shown) which detects the X-rays transmitted or scattered by an object (not shown) are multiplied by a suitable weighting factor. Subsequently, the X-ray beam moves from left to right in the range defined by the slit 9c.

Subsequently, the X-rays are switched off again, after which the aperture 13d and the slit 9d become operative. However, if the aperture 13c were previously situated on the other side (with respect to the radiation source 1) of the axis 5, the aperture 13d will now be situated between the axis 5 and the radiation source 1. The projection of the aperture 13d on the diaphragm body 3 is thus increased, but does not have a disturbing effect because the cross-section of the X-ray beam formed is defined exclusively by the dimensions of one of the slits 9a . . . 9e and the slit 8. The apertures 13a . . . 13e merely serve to pass the radiation through one of the slits.

After the X-ray beam has also traversed the range defined by the slit 9d, the slit 9e becomes operative for one half revolution, after the switching off of the X-rays; subsequently the slit 9a becomes operative etc. Thus, within five successive revolutions an X-ray beam emitted by the radiation source traverses the axial length of the diaphragm body 3 once. The apertures in the diaphragm body 12 may be distributed across its circumference in another manner, for as long as they are offset through 180°/n on the circumference with respect to neighbouring apertures and are adapted to the dimensions of a slit in the axial direction. However, spatially successive areas would not be successively traversed in time by the X-ray beam; instead the beam would jump, for example from the strip 9c to the strip 9e or otherwise in a similar manner.

The smaller the ratio of the diameter of the first diaphragm body 3 to the distance between the radiation source 1 and the axis of rotation 5, the less noticeable the alternating widening and narrowing of the X-ray beam described above will be. In cases where such "breathing" of the X-ray beam can be tolerated, it is not necessary to deactivate the radiation source 1 every other half revolution of the diaphragm body 3. In this case the second diaphragm body shown in the FIGS. 6 and 8 could also be used, be it that the X-ray beam would then jump from the slit 9a to the slit 9d and further to the slit 9b etc. However, the second diaphragm body 12 may then have an essentially simpler construction. In that case it would suffice to provide only a single helical wide slit which extends from the top left to the bottom right in FIG. 8. The width of the slit must be sufficient in order to allow for the X-ray beam to move within one of the slits 9a . . . 9e, but it should not be so large that two slits in the plane defined by focus 1 and axis can be simultaneously exposed to X-rays. In this case the first diaphragm aperture may also be provided with an even number of slits.

It is also possible to choose the diameter of the two diaphragm bodies so that the first diaphragm body comprising the slits is situated within the second diaphragm body. The described "breathing" of the X-ray beam in the case of continuously applied X-rays is then less pronounced; when the X-rays, however, are switched off after every other half revolution, it is generally more effective to choose the reverse device (first diaphragm body on the outside) shown in FIG. 4, because the X-ray beam emerging from the slits is then better defined.

What is claimed is:

1. A device for forming an X-ray beam or gamma ray beam of small cross-section and variable direction, comprising an X-ray source or gamma source which supplies a radiation beam and a diaphragm device which forms the X-ray beam from the radiation beam and which comprises a stationary diaphragm section provided with a rectilinear slit and a cylindrical first diaphragm body which rotates about an axis of rotation and which is provided with a helical slit on its outer surface, characterized in that the diaphragm body has an approximately semi-circular cross-section over at least a part of its length.

2. A device as claimed in claim 1, characterized in that the axis of rotation of the diaphragm body is situated in the plane defined by the radiation source and the rectilinear slit.

3. A device as claimed in claim 1, characterized in that the helical slit has a pitch which differs over the length of the diaphragm body.

4. A device as claimed in claim 1, characterized in that the slit is stepped.

5. A device as claimed in claim 1, characterized in that a plurality of helical slits succeed one another in the axial direction in the first diaphragm body.

6. A device as claimed in claim 5, characterized in that there is provided a second diaphragm body which comprises at least one aperture and which has a semi-circular section over at least a part of its length, the two diaphragm bodies being coaxially arranged so that one body encloses the other, the first diaphragm body rotating at a speed which is higher than that of the second diaphragm body as a function of the number of slits provided therein, the arrangement and the shape of the aperture on the circumference of the second diaphragm body being such that a usable beam can emerge through each time only one of the slits.

7. A device as claimed in claim 6, characterized in that the first diaphragm body encloses the second diaphragm body.

8. A device as claimed in claim 1, characterized in that the first diaphragm body is arranged between the radiation source and the diaphragm section (7).

9. A device as claimed in claim 6, characterized in that in the second diaphragm body there are provided n apertures n being the number of the slits in the first diaphragm body, the apertures being offset through an angle of 180°/n with respect to one another on the circumference, their axial position corresponding to the axial position of a respective a slit so that the radiation each time passes through one of the slits and through the associated aperture.

10. A device as claimed in claim 6, characterized in that in the second diaphragm body there is provided a sole aperture in the form of a helical slit which is substantially wider than the slits in the first diaphragm body and which extends through a circumferential angle of at least approximately 180°.

11. A device as claimed in claim 7, characterized in that in the second diaphragm body there are provided n apertures, n being the number of the slits in the first diaphragm body, the apertures being offset through an angle of 180°/n with respect to one another on the circumference, their axial position corresponding to the axial position of a respective slit so that the radiation each time passes through one of the slits (for example, 8b) and through the associated aperture.

12. A device as claimed in claim 2, characterized in that the slit is stepped.

13. A device as claimed in claim 2, characterized in that a plurality of helical slits succeed one another in the axial direction in the first diaphragm body.

14. A device as claimed in claim 2, characterized in that the helical slit has a pitch which differs over the length of the diaphragm body.

15. A device as claimed in claim 14, characterized in that the slit is stepped.

16. A device as claimed in claim 15, characterized in that a plurality of helical slits succeed one another in the axial direction in the first diaphragm body.

17. A device as claimed in claim 16, characterized in that there is provided a second diaphragm body which comprises at least one aperture and which has a semi-circular section over at least a part of its length, the two diaphragm bodies being coaxially arranged so that one body encloses the other, the first diaphragm body rotating at a speed which is higher than that of the second diaphragm body as a function of the number of slits provided therein, the arrangement and the shape of the aperture on the circumference of the second diaphragm body being such that a usable beam can emerge through each time only one of the slits.

18. A device as claimed in claim 17, characterized in that the first diaphragm body encloses the second diaphragm body.

19. A device as claimed in claim 18, characterized in that the first diaphragm body is arranged between the radiation source and the diaphragm section.

20. A device as claimed in claim 18, characterized in that in the second diaphragm body there are provided n apertures n being the number of the slits in the first diaphragm body, the apertures being offset through an angle of 180°/n with respect to one another on the circumference, their axial position corresponding to the axial position of a respective slit so that the radiation each time passes through one of the slits and through the associated aperture.

* * * * *